# United States Patent [19]

Huang

[11] 4,425,338

[45] Jan. 10, 1984

[54] NOVEL ALPHA-HETEROCYCLIC CARBINOL PHOSPHATES

[75] Inventor: Jamin Huang, Chapel Hill, N.C.

[73] Assignee: Union Carbide Corporation, Danbury, Conn.

[21] Appl. No.: 364,074

[22] Filed: Mar. 31, 1982

[51] Int. Cl.³ .................... A01N 57/16; A01N 57/32; C07D 263/56; C07D 263/14

[52] U.S. Cl. ...................... 424/200; 546/15; 546/22; 548/113; 548/119

[58] Field of Search ............ 548/113, 117, 119; 546/15, 22; 424/200

[56] References Cited

U.S. PATENT DOCUMENTS

| | | | |
|---|---|---|---|
| 2,877,155 | 3/1959 | Netivier | 548/113 |
| 3,674,803 | 7/1972 | Scherer et al. | 424/272 |
| 3,766,200 | 10/1973 | Rufenacht | 548/112 |
| 3,856,897 | 12/1974 | Fan | 548/119 |
| 3,890,336 | 6/1975 | Suzuki et al. | 424/200 |
| 4,062,951 | 12/1977 | Sauli | 424/200 |
| 4,137,308 | 1/1979 | Gutman | 424/200 |
| 4,209,515 | 6/1980 | Tomita et al. | 548/112 |

FOREIGN PATENT DOCUMENTS

| | | |
|---|---|---|
| 647745 | 8/1964 | Belgium . |
| 1161275 | of 1964 | Fed. Rep. of Germany . |
| 1267466 | 5/1968 | Fed. Rep. of Germany . |
| 1162422 | 9/1958 | France . |
| 2168184 | 10/1973 | France . |
| 2193022 | 2/1974 | France . |
| 49-00442 | 1/1974 | Japan . |
| 49-11623 | 11/1974 | Japan . |
| 52-76436 | 6/1977 | Japan . |
| 6607822 | 12/1966 | Netherlands . |
| 932388 | 7/1963 | United Kingdom . |

OTHER PUBLICATIONS

Pianka et al., J. Sci. Food Agr., 1968, v. 19, pp. 399–402, 403–408.

Primary Examiner—Richard Raymond
Attorney, Agent, or Firm—John A. Shedden

[57] ABSTRACT

Novel alpha-heterocyclic carbinol phosphates have been found to exhibit insecticidal and miticidal activity.

30 Claims, No Drawings

ALPHA-HETEROCYCLIC CARBINOL PHOSPHATES

This invention relates to novel insecticidal and miticidal alpha-heterocyclic carbinol phosphates. This invention also relates to pesticidal compositions for controlling insects and mites, as well as to methods of controlling insects and mites by subjecting them to an insecticidally or miticidally effective amount of the compounds of this invention.

The novel compounds of this invention are compounds of the formula:

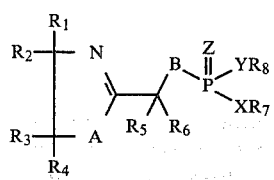

wherein:
A is O, S or $NR_9$;
$R_9$ is hydrogen or $C_1$ to $C_6$ alkyl;
B is O, S or NH;
X is O or S;
Y is S or NH;
Z is O or S;
$R_7$ and $R_8$ are individually $C_1$ to $C_6$ alkyl;
$R_1$, $R_2$, $R_3$ and $R_4$ are individually hydrogen, alkyl, haloalkyl, alkenyl, alkynyl, cycloalkyl, cycloalkenyl, aryl, aryl substituted with one or more nitro, halogen, alkyl, trifluoroalkyl, cyano, alkoxy, and alkylthio groups; or
$R_1$ and $R_3$, $R_2$ and $R_4$ are together or independently a cyclic ring of 3–6 atoms; or
$R_1$ and $R_2$, $R_3$ and $R_4$ are together or independently a cyclic ring of 4–6 atoms; or
$R_1$, $R_2$, $R_3$ and $R_4$ together form a 6-membered aromatic ring which is non-substituted or alkyl; halo, alkoxy, alkylthio, alkylamino or dialkylamino substituted alkyl; alkoxy, alkylthio, halo, nitro, cyano, trifluoromethyl, phenoxy, trifluoromethoxy, phenylthio, alkoxycarbonyl, alkylaminocarbonyl, dialkylaminocarbonyl, alkanoyl, aroyl, alkenyl or alkynyl substituted; or
$R_2$ and $R_4$ is a chemical bond and $R_1$ and $R_3$ is alkoxy, alkylthio, nitro, cyano, phenoxy, halogen, or phenylthio,
$R_5$ is hydrogen, cyano, alkyl, alkenyl, halo-alkenyl, cycloalkenyl, or alkynyl; non-substituted pyridyl, 2-benzothiazole, 2-benzoxazole, furanyl, or thiophenyl; or halo, nitro, cyano, trifluoromethyl, alkyl, alkoxy, alkoxycarbonyl, alkylaminocarbonyl, trifluoromethoxy, dialkylaminocarbonyl, alkanoyl or aroyl substituted pyridyl, 2-benzothiazole, 2-benzoxazole, furanyl, or thiophenyl; or non-substituted aryl;
or alkyl, halo, alkoxy, alkylthio, alkylamino or dialkylamino substituted alkyl; alkoxy, alkylthio, halo, nitro, cyano, trifluoromethyl, phenoxy, phenylthio, alkoxycarbonyl, alkylaminocarbonyl, dialkylaminocarbonyl, alkanoyl, aroyl, alkenyl or alkynyl substituted aryl;
$R_6$ is non-substituted aryl or alkyl, alkylthio, alkoxy, halo, nitro, cyano, alkylamino, dialkylamino, trifluoromethyl, phenoxy, phenylthio, alkoxycarbonyl, trifluoromethoxy, alkylaminocarbonyl, dialkylamino carbonyl, alkanoyl, aroyl, alkenyl or alkynyl substituted aryl.

Generally, the preferred compounds of this invention are those wherein:
A is O or S;
X is O;
Y is S;
$R_1$, $R_2$, $R_3$ and $R_4$ together form a 6-membered aromatic ring which is non-substituted or alkyl or halo, alkoxy, alkylthio, alkylamino or dialkylamino substituted alkyl; alkoxy, alkylthio, halo, nitro, cyano, trifluoromethyl, phenoxy, phenylthio, alkoxycarbonyl, alkylaminocarbonyl, dialkylaminocarbonyl, alkylaminocarbonyl, dialkylaminocarbonyl, alkanoyl, aroyl, alkenyl or alkynyl substituted; and
$R_5$ is hydrogen;

Generally, the more preferred of the preferred compounds of this invention are those wherein:
B is oxygen;
$R_6$ is a halo-substituted aromatic ring;
$R_8$ is n-propyl; and
$R_7$ is ethyl.

The most preferred compounds of this invention are the following:
O-[alpha-(2-benzothiazolyl)-2-chlorobenzyl]-O-ethyl-S-n-propyl thiophosphate.
O-[alpha-(2-benzothiazolyl)-2,4-dichlorobenzyl]-O-ethyl-S-n-propyl thiophosphate.
O-[alpha-(2-benzoxazolyl)-2-chlorobenzyl]-O-ethyl-S-n-propyl thiophosphate.
O-[alpha-(2-benzoxazolyl)-2,4-dichlorobenzyl]-O-ethyl-S-n-propyl thiophosphate.
O-[alpha-(2-benzoxazolyl)-3,4-dichlorobenzyl]-O-ethyl-S-n-propyl thiophosphate.
O-[alpha-(2-benzoxazolyl)-2,6-dichlorobenzyl]-O-ethyl-S-n-propyl thiophosphate.
O-[alpha-(2-benzothiazolyl)-2-nitrobenzyl]-O-ethyl-S-n-propyl thiophosphate.

The novel alpha-heterocyclic carbinol phosphates of this invention can be conveniently prepared by the general reaction methods or modifications thereof set forth below. The preparation can consist of two steps: step one consists of the preparation of appropriate alcohols, thiols and amines; step two consists of a phosphorylation reaction.

In the following methods,
A, B, Z, Y, X, $R_1$, $R_2$, $R_3$, $R_4$, $R_5$, $R_6$, $R_7$ and $R_8$ are as described previously;
$X^1$ is $OCH_3$, $OCH_2CH_3$, Cl, or

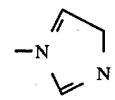

$Y^1$ is $Li^\oplus$, $Na^\oplus$ or $MgBr^\oplus$
Q may be Cl, Br,

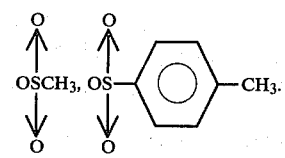

M⊕ may be alkali metal, alkaline earth metal or ammonium cation or a cation of an organic base.

Step one, the preparation of appropriate alcohols and/or thiols, can be achieved by the following methods.

METHOD I

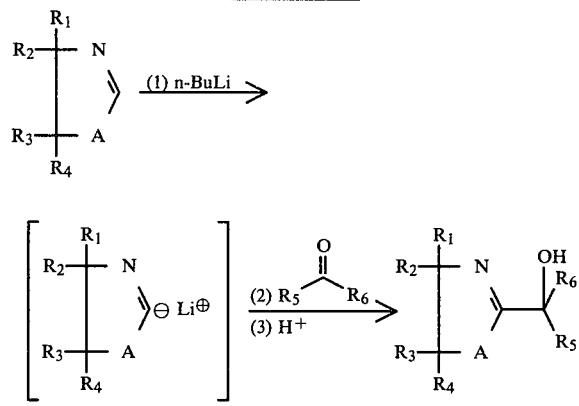

The substituted 2-(4,5-dihydro-1,3-azole) methanols and 2-(1,3-azole) methanols illustrated in Method I can be effected by metallation of 4,5-dihydro-1,3-azoles and 1,3-azoles with one equivalent of n-butyllithium at −78° C., followed by the addition of appropriate aldehydes or ketones. This reaction may be performed in anhydrous diethyl ether or tetrahydrofuran.

METHOD II

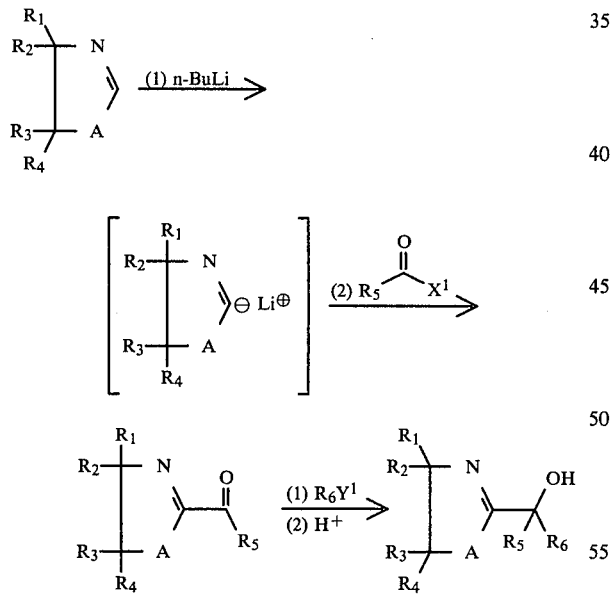

The preparation of ketones or aldehydes in Method II can be achieved by metallation of 4,5-dihydro-1,3-azoles and 1,3-azoles as described in Method I, followed by the addition of appropriate methyl esters (or ethyl esters, acid chlorides, acyl imidazoles, alkyl nitrile, phenylnitrite). The desired carbinols can then be effected by nucleophilic addition of appropriate organometallic compounds (such as alkyllithium, phenyllithuim, Grignard reagents) or nitrile ion toward the ketones or aldehydes.

METHOD III

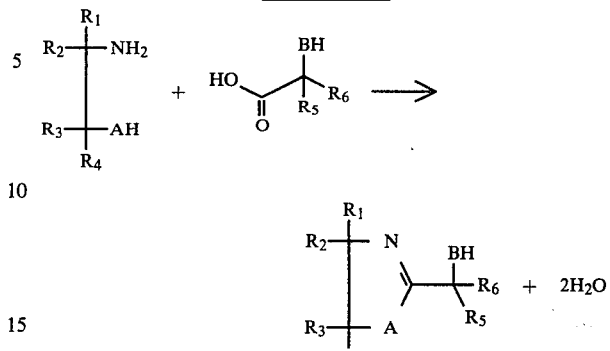

The condensation reaction outlined in Method III can be accomplished using essentially equimolar ratios of the alpha-hydroxy acids (or alpha-thio acids) and appropriate 2-aminoethanols (or 2-aminoethanethiols, 1,2-diaminoethanes, O-aminophenols, O-aminothiophenols, O-aminoanilines) in a variety of conditions. This may be effected by azeotropically removing water via an inert, high-boiling organic solvent such as xylene. It can also be achieved by refluxing the two components in aqueous hydrochloric acid solution or heating the two reagents in a sealed tube at an elevated temperature.

METHOD IV

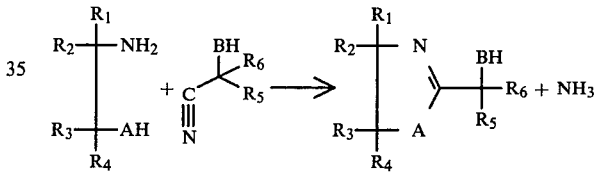

The reaction of Method IV can be conducted using equimolar ratios of the alpha-hydroxynitrile (or alpha-thio nitrile) and appropriate 2-aminoethanols, (or 2-aminoethanethiols, 1,2diaminoethanes, O-aminophenols, O-aminothiophenols, O-aminoanilines) in refluxing methanol.

METHOD V

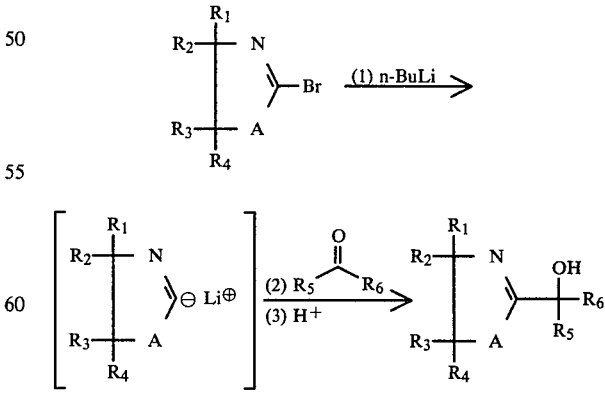

The reaction as outlined in Method V can be accomplished by halogen-lithium exchange of 2-bromo-1,3-azoles or 2-bromo-4,5-dihydro-1,3-azoles with one equivalent of n-butyllithium at −78° C. The corresponding lithium anion can then react with a variety of aldehydes or ketones to form desired alcohols. This reaction can be performed in anhydrous diethylether or tetrahydrofuran.

Preparation of appropriate amines can be achieved by the following reaction schemes.

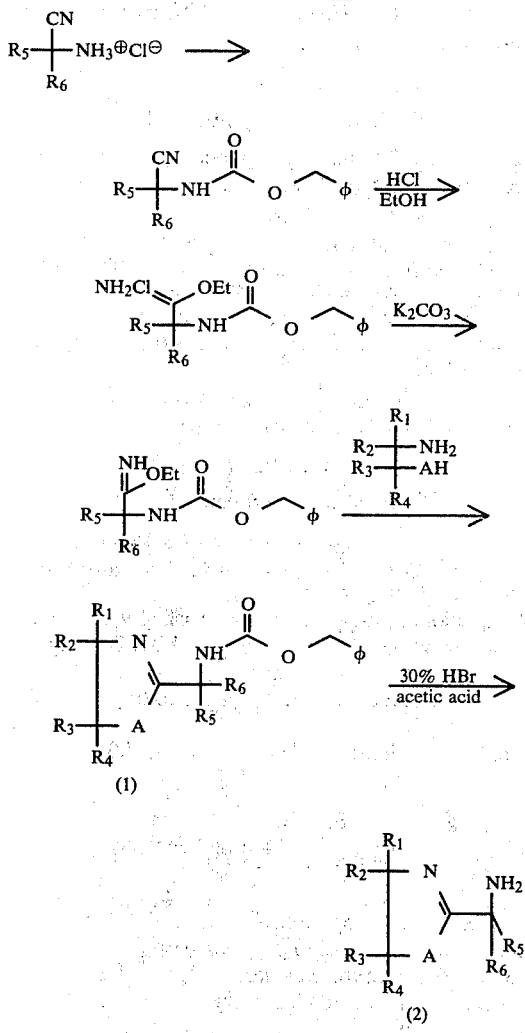

The reaction scheme illustrated in Method VI can be effected by protecting the alpha-amino nitrile with a benzyloxycarbonyl group. The nitrile is treated with dry hydrogen chloride in a mixture of alsolute ethanol and absolute ether to yield the corresponding iminoether hydrochloride. Free iminoether can be obtained from the hydrochloride by removal of hydrogen chloride by treatment with aqueous concentrated potassium carbonate solution. Coupling of the iminoether with appropriate 2-aminoethanols (or 2-aminoethane thiols, 1,2-diaminoethanes, O-aminophenols, O-aminothiophenols, O-aminoanilines) gives protected amine (1) which can then be treated with 30% hydrogen bromide in acetic acid to afford the desired amine hydrobromide (2).

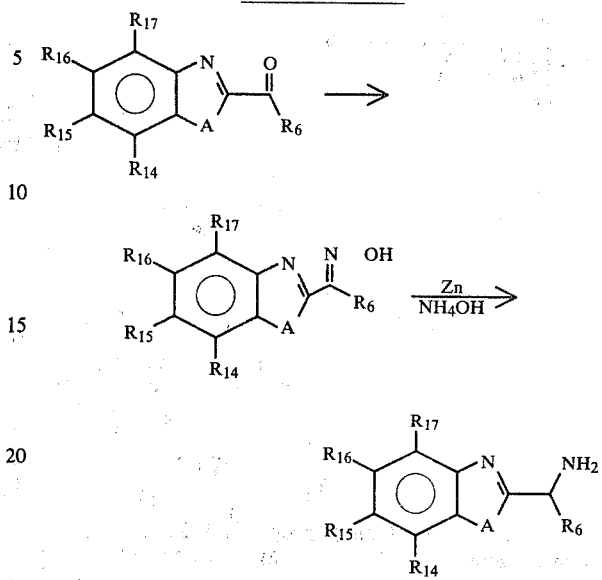

$R_{14}$ through $R_{17}$ are the substituents defined under the preferred compounds of this invention, i.e., when $R_1$ through $R_4$ form a six-membered aromatic ring.

The reaction scheme outlined in method VII demonstrates the preparation of amines. It can be achieved by the formation of appropriate oxime, followed by reduction with powdered zinc in aqueous ammonia.

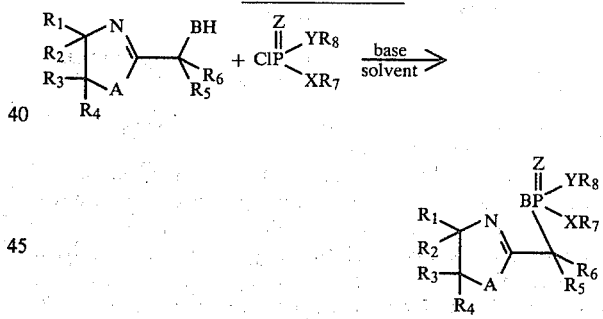

The phosphorylation illustrated in Method VIII can be achieved by reaction with appropriate phosphorylating agent in the presence of acid acceptor. Suitable acid acceptors are tertiary amine bases such as triethylamine or pyridine or preferably N, N'-dimethyl-4-aminopyridine. This reaction may be performed in a variety of organic solvents including methylene chloride, ethyl acetate, acetonitrile. This reaction can be conducted with temperatures ranging from 20° C. to 50° C. The resulting phosphates are viscous oils which are normally purified by Florisil chromatography (100–200 mesh) eluting with 4% ethyl acetate in hexane and increasing solvent polarity with ethyl acetate.

The preparation of these phosphates may also be achieved as shown in Method IX, by reacting salts of appropriate phosphoric acid of formula 3 with 4 in a variety of solvents. Illustrative of these organic solvents are methanol, ethanol and acetone.

METHOD IX

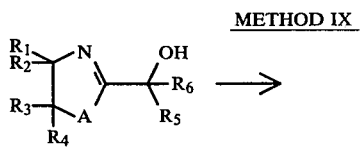

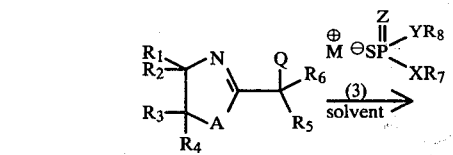

In general, the alcohols prepared in Methods I to V and the amines synthesized in Methods VI and VII are known compounds or can be prepared in accordance with conventional methods known to those skilled in the art.

The phosphorous halides and the salts of the phoshoric acid in Methods VII and IX respectively generally are known materials in the art and can be obtained from commercial sources or prepared in accordance with conventional methods known to those skilled in the art.

The following examples are illustrative of the methods of preparing the novel compounds of this invention.

EXAMPLE I 2-(O-chloro-alpha-hydroxybenzyl)-4.4-dimethyloxazoline 4.4-Dimethyl-2-oxazoline (12.5 g.) in 200 ml. of diethyl ether under nitrogen was cooled to $-78°$ C. and 83 ml. of 1.6 M n-butyllithium in hexane was added dropwise at $-78°$ C. The white suspension mixture was stirred at $-78°$ C. for 30 minutes. To this suspension mixture was added a solution of O-chlorobenzaldehyde (19 g.) and 50 ml. of diethyl ether at $-78°$ C. and stirred at $-78°$ C. for 2 hours under nitrogen. The suspension mixture was allowed to warm to room temperature and stirred overnight.

The mixture was quenched by the addition of 10% NH$_4$Cl aqueous solution (200 ml.) and extracted with three portions of diethyl ether. The combined either extracts were washed with brine, dried over Na$_2$SO$_4$, filtered and concentrated in vacuo to yield 18 g. of light yellow solid. Recrystallization from hexane afforded 7.5 g. of white crystal, mp 120°-122° C.

Anal. $C_{12}H_{14}ClNO_2$: Calc: C, 60.13; H, 5.89; N, 5.84. Found: C, 59.88; H, 5.83; N, 5.64.

EXAMPLE II 2-(O-choloro-alpha-hydroxybenzyl)benzothiazole 47 ml. of 1.6 M n-butyllithium in hexane was added dropwise to the solution of benzothiazole (10 g.) and diethyl ether (200 ml.) at $-78°$ C. for 30 minutes, followed by the addition of a solution of O-chlorobenzaldehyde (10.8 g.) and diethyl ether (100 ml.) at $-78°$ C. The mixture was then stirred at $-78°$ C. for 2 hours before it was allowed to warm to room temperature and stirred at room temperature overnight.

The mixture was then quenched by the addition of 7.5% NH$_4$Cl aqueous solution (250 ml.) and extracted with three portions of diethyl ether. The combined ether extracts were washed with brine, dried over Na$_2$SO$_4$, filtered and concentrated in vacuo to yield a yellow solid. Recrystallization from hexane and ethyl acetate afforded 9.9 g. of yellow needle crystals, mp. 118°-120° C.

Anal. $C_{14}H_{10}ClNOS$: Calc: C, 60.97; H, 3.66; N, 5.08. Found: C, 61.05; H, 3.55; N, 5.09.

EXAMPLE III 2-(alpha-hydroxybenzyl)-benzothiazole

A mixture of O-aminothiophenol (23.5 g.) and dl-mandelic acid (25 g.) was refluxed in xylene with a Dean-Stark tube for two days.

After cooling, the solution was washed with 1 N HCl aqueous solution (500 ml.), 5% Na$_2$CO$_3$ aqueous solution (500 ml.) and brine. It was dried over MgSO$_4$, filtered and concentrated in vacuo to yield a solid residue. Recrystallization from toluene afforded 16.6 g. of white crystal.

Anal. $C_{14}H_{11}NOS$: Calc: C, 69.68; H, 4.60; N, 5.81. Found: C, 70.10; H, 4.63; N, 5.78.

EXAMPLE IV 2-(alpha-thioethyl)-benzoxazole

A mixture of thiolactic acid (18.7 g.) and O-aminophenol (17.5 g.) was refluxed in xylene with a Dean-Stark tube overnight.

After cooling, the solution was washed with 1 N HCl aqueous solution (2×500 ml.), 5% NaHCO$_3$ aqueous solution (2×500 ml.) and brine. It was dried over Na$_2$SO$_4$, filtered and concentrated in vacuo to yield desired product (8 g.).

Anal. $C_9H_9HOS$: Calc: C, 60.30; H, 5.06; N, 7.82. Found: C, 60.90; H, 5.09; N, 7.67.

EXAMPLE V 2-(alpha-aminobenzyl)-benzothiazole

Ethyl benzoate (60.1 g., 0.4 mol.) in 200 ml. of diethyl ether was added dropwise to 0.4 mol. benzothiazolyllithium in 700 ml. of diethyl ether (see Example II) at $-78°$ C., the mixture was stirred 2 hours at $-78°$ C., and room temperature overnight. It was quenched by the addition of 10% NH$_4$Cl aqueous solution and extracted with three portions of diethyl ether. The combined ether extracts were washed with brine, dried over Na$_2$SO$_4$, filtered, concentrated in vacuo and recrystallized from hexane and ethyl acetate to affort 41.5 g. of light-brown crystal (phenyl 2-benzothiazolyl ketone).

A mixture of the phenyl 2-benzothiazolyl ketone (35 g.), hydroxyamine hydrochloride (10.5 g.), pyridine (175 ml.) and ethanol (175 ml.) was refluxed for 4 hours. After cooling, the solution was concentrated in vacuo 36.6 g. of oxime was obtained.

A mixture of the oxime (21.6 g.), aqueous ammonia (800 ml.) and ethanol (80 ml.) was stirred with 16.7 g. of powdered zinc at 50°-60° C. for 30 minutes, another 9.5 g. of powdered zinc was then added. The suspension was stirred at 50°-60° C. for 4 hours.

After cooling, the gray suspension mixture was extracted with three portions of methylene chloride. The combined methylene chloride extracts were dried over Na₂SO₄, filtered and concentrated in vacuo. Immediately after the addition of 1 N HCl (200 ml.) to the residue, yellowish white solid was formed. It was filtered, washed with water and then methylene chloride. 19.5 g. Of 2-(alpha-aminobenzyl)-benzothiazole hydrochloride as white solid was obtained.

The hydrochloride was dissolved with aqueous ammonia and methylene chloride, the aqueous layer was extracted with two portions of methylene chloride. The combined methylene chloride extracts were washed with brine, dried over Na₂SO₄, filtered and concentrated in vacuo. 13.1 g. of white solid of desired producted was obtained, mp. 68°–70° C.

Anal. $C_{14}H_{12}N_2S$: Calc: C, 69.96; H, 5.03; N, 11.66. Found: C, 69.88; H, 5.18; N, 11.55.

EXAMPLE VI

O-2-(O,p-dichloro-alpha-hydroxybenzyl)benzoxazole-O-ethyl-S-n-propylthiophosphate A mixture of O-ethyl-S-n-propyl phosphorochloridate (5.2 g.) and methylene chloride (15 ml.) was added to the solution of 2-(o,p-dichloro-alpha-hydroxybenzyl)-benzoxazole (5 g.), N, N-dimethyl-4-aminopyridine (2.3 g.), triethylamine (2.6 ml.) and methylene chloride (75 ml.) at room temperature, and refluxed with a drying tube for two days.

The solution was cooled to room temperature, and washed with water, dried over Na₂So₄, filtered and concentrated in vacuo. The crude viscous residue was chromatographed on a Florisil (100–200 mesh, 170 g.) utilizing a hexane-ethyl acetate increasing polarity gradient. The desired phosphate (2.1 g.) as viscous oil was afforded, $N_d^{20°}$: 1.6370.

Anal. $C_{19}H_{20}Cl_2NO_4PS$: Calc: C, 49.57; H, 4.38; N, 3.04. Found: C, 49.91; H, 4.51; N, 3.96.

The following compounds are illustrative of this invention, all of which can be conveniently prepared by the processes of this invention simply by selecting appropriate starting materials.

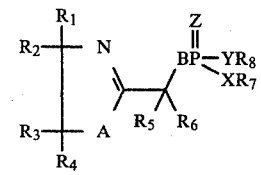

| A | B | Z | X | Y | R₁ | R₂ | R₃ | R₄ | R₅ | R₆ | R₇ | R₈ |
|---|---|---|---|---|---|---|---|---|---|---|---|---|
| O | O | O | O | S | CH₃ | CH₃ | H | H | H | ⟨C₆H₄⟩-Cl | Et | n-Pr |
| O | NH | O | O | S | Cl | — | Cl | — | H | ⟨C₆H₄⟩-SCH₃ | Et | i-Butyl |
| S | O | O | O | S | —(CH₂)₅— | | H | H | H | 2,3-Cl₂-C₆H₃ | Et | n-Pr |
| O | O | O | O | S | C₆H₅ | — | H | — | H | CH₃-C₆H₄-O-C₆H₅ | Et | Et |
| S | O | O | O | NH | Cl | — | Cl | — | H | C₆H₅-S(O)₂-CH₃ | Et | i-Pr |
| S | O | O | O | S | H | — | H | — | H | C₆H₄-NO₂ | Et | n-Pr |

| A | B | Z | X | Y | R'₁ | R'₂ | R'₃ | R'₄ | R₅ | R₆ | R₇ | R₈ |
|---|---|---|---|---|---|---|---|---|---|---|---|---|
| S | NH | O | O | S | H | CF₃ | H | Cl | C₆H₅ | H | Et | n-Pr |

-continued

[Structure: benzoxazole-type compound with substituents R9-R17, and BP(=Z)(SR8)(OR7) group, with core atoms A and B]

| A | B | Z | R9 | R10 | R11 | R12 | R13 | R14 | R15 | R16 | R17 | R7 | R8 |
|---|---|---|----|-----|-----|-----|-----|-----|-----|-----|-----|----|----|
| S | O | O | Cl | H | Cl | H | H | H | H | H | H | Et | n-Pr |
| O | O | O | Cl | H | H | H | Cl | H | H | H | H | Et | n-Pr |
| O | S | O | NO$_2$ | H | H | H | H | Cl | H | Cl | H | Et | n-Pr |
| S | O | S | H | Cl, −O−⟨phenyl⟩−Cl | H | H | H | CF$_3$ | H | Cl | H | Et | n-Pr |
| O | NH | S | H | H | −N(CH$_3$)$_2$ | H | H | H | H | ⟨phenyl⟩ | H | Et | Et |
| S | S | O | Cl | H | Cl | H | Cl | H | CF$_3$ | H | CF$_3$ | Et | n-Pr |
| O | O | O | H | −S(=O)(=O)CH$_3$ (S↑O↓O arrow structure) | H | H | H | H | H | −SO$_2$CH$_3$ | H | Et | i-Pr |
| S | O | O | H | Cl | Cl | H | H | H | H | NO$_2$ | H | Et | n-Pr |
| O | O | S | H | H | −C≡C−CH$_3$ | H | H | H | H | Br | H | Et | n-Pr |
| O | O | O | H | CH$_2$OCH$_3$ | H | H | H | H | H | −C(=O)CH$_3$ | H | Et | i-Butyl |
| S | NH | O | H | H | −C≡N | H | H | H | H | OCH$_3$ | H | n-Pr | n-Pr |
| O | O | O | NO$_2$ | H | NO$_2$ | H | H | Cl | H | CF$_3$ | H | Et | n-Pr |
| S | S | O | CF$_3$ | H | CF$_3$ | H | H | H | Cl | NO$_2$ | H | Et | n-Pr |
| O | O | S | H | OCH$_3$ | H | H | H | H | H | −C(=O)OCH$_3$ | H | Et | n-Butyl |
| O | O | O | Cl | H | CF$_3$ | H | H | Cl | Cl | Cl | Cl | Et | n-Pr |
| S | O | O | Cl | H | H | H | H | NO$_2$ | H | NO$_2$ | H | Et | n-Pr |

Selected species of the new compounds were evaluated to determine their pesticidal activity against mites, mite eggs, an aphid, a caterpiller, a beetle, and a fly.

Suspensions of the test compounds were prepared by dissolving one gram of compound in 50 ml. of acetone in which had been dissolved 0.1 g. (10 percent of the weight of the compound) of an alkylphenoxy polyethoxyethanol surfactant, as an emulsifying or dispersing agent. The resulting solution was mixed into 150 ml. of water to given roughly 200 ml of a suspension containing the compound in finely divided form. The thus-prepared stock suspension contained 0.5 percent by weight of compound. The concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae* Scop.) reared on potted dwarf nasturtium plants at 68°–70° F. and 50±5 percent relative humidity, constituted the test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids were placed on a revolving turntable and sprayed with 100–110 milliliters of test compound formulation by use of a Devilbiss spray gun set at 40 psig air pressure. This application, which lasted 25 seconds, was sufficient to wet plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 68°–70° and 50±5 percent, respectively. Aphids which fell onto the paper and were unable to remain standing after being uprighted were considered dead. Aphids remaining on the plant were observed closely for movement and those which were unable to move the length of the body upon stimulation by prodding were considered dead. Percent mortality was recorded for various concentration levels.

Southern Armyworm Leaf Spray Bait Test

Larvae of the southern armyworm (*Spodoptera eridania*, (Cram.)), reared on Tendergreen bean plants at a temperature of 85+5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulations by use of a DeVilbiss spray gun set at 40 psig air pressure. This application, which lasted 25 seconds, was sufficient to wet plants to run-off. As a control, 100–110 milliliters of a water-ace-tone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labled and held at 80°–85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis*, Muls.), reared on Tendergreen bean plants at a temperature of 80±5 F. and 50±5 percent relative humidity, were the test insects.

The test compounds were formulated by diluting the stock suspension with water to give a suspension containing 500 parts of test compound per million parts of final formulation. Tendergreen bean plants of standard height and age were placed on a revolving turntable and sprayed with 100–110 milliliters of test compound formulation by use of a DeVilbiss spray gun set at 40 psig air pressure. This application, which lasted 25 seconds, was sufficient to wet plants to run-off. As a control, 100–110 milliliters of water-acetone-emulsifier solution containing no test compound were also sprayed on infested plants. When dry, the paired leaves were separated and each was placed in a 9 centimeter Petri dish lined with moistener filter paper. Five randomly selected larvae were introduced into each dish, and the dishes were closed. The closed dishes were labeled and held at a temperature of 80+5 F., for three days. Although the larvae could easily consume the leaf within 24 to 48 hours, no more food was added. Larvae which were unable to move the length of the body even upon stimulation, were considered dead.

Southern Armyworm Ovicide Test

The test organism was the egg of the Southern armyworm (*Spodoptera eridania* (Cram.)) as obtained from adults reared on Tendergreen bean plants at a temperature of 80°±5° F. and a relative humidity of 50±5 percent. The eggs were laid on freezer paper (Marlon 717, Copco paper). The paper was then cut into small sections containing one or two egg masses.

The test compounds were formulated by diluting the stock suspension with water to give a suspension containing 500 parts of test compound per million parts of final formulation. The egg masses were dipped until they were thoroughly wet (5–10 seconds). They were then placed on a paper towel face up and were allowed to dry for 15–30 minutes. The dry eggs were placed in a 15×60 mm petri dish containing a cotton dental wick saturated with a 5 percent sodium chloride solution to maintain a high level of humidity. The closed dishes were labeled and held at a temperature of 80°±5° F. for four days. Larvae that emerged from the eggs, even if dead at the time of observation, were recorded as hatched.

Mite Foliage Spray Test

Adults and nymphal stage of the two-spotted mite (*Tetranychus urticae* Koch), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150–200 mites, a sufficient number for testing, were transferred from the excised leaves to the fresh plants in a period of twenty-four hours. Following the twenty-four hour transfer period, the excised leaves were removed from the infested plants. The test compounds were formulated by diluting the stock suspension with water to given a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig. air pressure. This application, which last 25 seconds, was sufficient to wet the plants to run-off. As a control, 100–110 milliliters of a water solution containing acetone and emulsifier in the same concentrations as the test compound formulations, but containing no test compound, were also sprayed on infested plants. The sprayed plants were held at 80±5 percent relative humidity for six days, after which a mortaility count of motile forms was made. Microscopic examination for motile forms was made on the leaves of the test plants. Any individual which was capable of locomotion upon prodding was considered living.

Fly Bait Test

Four to six day old adult house flies (*Musca domestica*, L.), reared according to the specifications of the Chemical Specialties Manufacturing Assocation (Blue Book, McNair-Dorland Co., N.Y. 1954; pages 243–244, 261) under controlled conditions of 80°±5° F. and 50±5 percent relative humidity, were the test insects. The flies were immobilized by anesthetizing with carbon dioxide and twenty-five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten millilters of the test formulation were added to a souffle cup containing a one-inch square of an absorbent cotton pad. This bait cup was introduced and centered on the blotting paper under the food strainer prior to admitting the anesthetized flies. The caged flies were allowed to feed on the bait for twenty-four hours, at a temperature of 80±5° F. and a relative humidity of 50±5 percent. Flies which showed no sign of movement on prodding were considered dead.

The results of these tests together with physical properties of the tested compounds are set forth in Table I below. In these tests the pesticidal activity of the compounds at the indicated dosage rate against aphid, mite, Southern Armyworm, Bean Beetle, and housefly was rated as follows:

A=excellent control (complete kill) at 500 ppm.
B=partial control (moderate kill) at 500 ppm.
C=no control (little or no kill) at 500 ppm.

The compounds contemplated in this invention may be applied as insecticides and miticides according to methods known to those skilled in the art. Pesticidal compositions containing the compounds as the active toxicant will usually comprise a carrier and/or diluent, either liquid or solid.

Suitable liquid diluents or carriers include water, petroleumn distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the acid of suitable surface active emulsifying and dispersing agents.

The choice of dispersing and emulsifying agents and the amount employed is dicated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Non-ionic, anionic, amphoteric, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder, dust or granulated composition, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein control the population of insects, mites, and of ova mites and insects upon plants or other material to which the pesticides are applied. Generally, when used in sufficient amount for kill or repel the insects, they do not burn or injure the plant. The toxicants are compatible with substantially any other constituents of the spray schedule, and they may be used in the soil, upon the seeds, or the roots of plants without injuring either the seeds or roots of plants. They may also be used in combination with other pesticidally active compounds.

TABLE I

| | | BIOLOGICAL AND ANALYTICAL PROPERTIES OF THE COMPOUNDS OF THIS INVENTION | | | | |
|---|---|---|---|---|---|---|
| | | BIOLOGICAL ACTIVITY | | | | |
| STRUCTURE | ANALYTICAL | TWO BEAN APHID | SPOTTED MITE | MEXICAN SOUTHERN ARMYWORM | BEAN BEETLE | HOUSE FLY |
| (structure 1) | $C_{15}H_{22}NO_3PS_2$<br>Calc: C, 50.12; H, 6.17; N, 3.58<br>Found: C, 51.41; H, 6.37; N, 5.44<br>Oil | C | A | B | A | C |
| (structure 2) | $C_{15}H_{19}NO_3PS_2$<br>Calc: C, 45.97; H, 4.89; N, 3.57<br>Found: C, 46.72; H, 5.16; N, 3.80<br>Oil | C | C | C | C | A |
| (structure 3) | $C_{17}H_{25}ClNO_4PS$<br>Calc: C, 50.30; H, 6.21; N, 3.45<br>Found: C, 52.33; H, 6.81; N, 4.80<br>Oil | A | A | B | A | B |

TABLE I-continued
BIOLOGICAL AND ANALYTICAL PROPERTIES OF THE COMPOUNDS OF THIS INVENTION

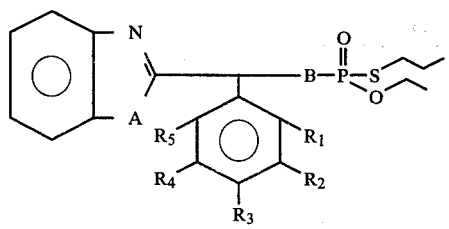

| STRUCTURE | | | | | | | | BIOLOGICAL ACTIVITY | | | | |
|---|---|---|---|---|---|---|---|---|---|---|---|---|
| A | B | $R_1$ | $R_2$ | $R_3$ | $R_4$ | $R_5$ | ANALYTICAL | TWO BEAN APHID | SPOTTED MITE | MEXICAN SOUTHERN ARMYWORM | BEAN BEETLE | HOUSE FLY |
| O | O | H | H | H | H | H | $C_{19}H_{22}NO_4PS$ Calc: C, 58.30; H, 5.67; N, 3.58 Found: C, 57.67; H, 5.98; N, 3.81 Oil | A | A | A | A | B |
| O | O | Cl | H | H | H | H | $C_{19}H_{21}ClNO_4PS$ Calc: C, 53.98; H, 4.97; N, 3.29 Found: C, 55.48; H, 4.85; N, 3.63 Oil | A | A | A | A | A |
| O | O | Cl | H | Cl | H | H | $C_{19}H_{20}Cl_2NO_4PS$ Calc: C, 49.57; H, 4.38; N, 3.04 Found: C, 49.91; H, 4.51; N, 2.96 Oil | A | A | A | A | A |
| O | O | H | Cl | Cl | H | H | $C_{19}H_{20}Cl_2NO_4PS$ Calc: C, 49.57; H, 4.38; N, 3.04 Found: C, 49.31; H, 4.44; N, 3.00 Oil | A | A | A | A | A |
| S | O | H | H | H | H | H | $C_{19}H_{21}NO_3PS_2$ Calc: C, 56.00; H, 5.44; N, 3.44 Found: C, 55.91; H, 5.51; N, 3.59 Oil | C | A | A | A | C |
| S | O | CL | H | H | H | H | $C_{19}H_{21}ClNO_3PS_2$ Calc: C, 51.63; H, 4.97; N, 3.17 Found: C, 51.77; H, 4.80; N, 3.15 Oil | A | A | A | A | A |
| S | O | Cl | H | Cl | H | H | $C_{19}H_{20}Cl_2NO_3PS_2$ Calc: C, 47.90; H, 4.23; N, 2.94 Found: C, 47.50; H, 4.39; N, 3.87 Oil | A | A | A | A | A |
| S | NH | H | H | H | H | H | $C_{19}H_{23}N_2O_2PS_2$ Calc: C, 56.13; H, 5.70; N, 6.89 Found: C, 55.39; H, 5.78; N, 7.10 Oil | C | C | C | C | C |
| S | O | $NO_2$ | H | H | H | H | $C_{19}H_{21}NO_5PS_2$ Calc: C, 52.04; H, 4.83; N, 3.19 Found: C, 50.77; H, 4.65; N, 6.24 Oil | B | A | A | A | A |

TABLE II
COMPARATIVE BIOLOGICAL PROPERTIES OF THE COMPOUNDS OF THIS INVENTION

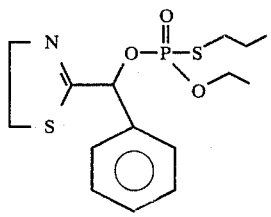

| | BEAN APHID | TWO SPOTTED MITE | SOUTHERN ARMYWORM | MEXICAN BEAN BEATLE | HOUSE FLY |
|---|---|---|---|---|---|
| | i | 120 | 500 | 190 | i |

TABLE II-continued
COMPARATIVE BIOLOGICAL PROPERTIES OF THE COMPOUNDS OF THIS INVENTION

| | BEAN APHID | TWO SPOTTED MITE | SOUTHERN ARMYWORM | MEXICAN BEAN BEATLE | HOUSE FLY |
|---|---|---|---|---|---|
| (structure) | 300 | 65 | 240 | 80 | i |
| (structure) | 65 | 15 | 50 | 25 | 110 |
| (structure) | 90 | 13 | 70 | 31 | 200 |

(i = inactive)

$LD_{50}$ (ppm) is the concentration in parts per million that will give 50% kill of a given population. The test procedures are identical to those previously described except that the concentration of toxicant is varied Table II illustrates that the activity of the phosphates derived from benzothiazole and benzoxazole are comparable and that the phosphates with the benzothiazole moiety are considerably more active than the corresponding phosphates with non-aromatic thiazoline moiety.

Table II also illustrates the significantly enhanced activity realized with halogen substitution on the carbinol phenyl substituent.

TABLE III

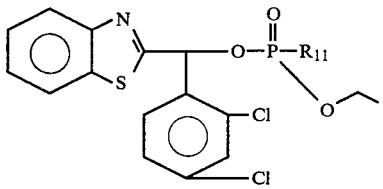

| | LD$_{50}$ (ppm) | | | | |
|---|---|---|---|---|---|
| $R_{11}$ | BEAN APHID | TWO SPOTTED MITE | SOUTHERN ARMYWORM | MEXICAN BEAN BEETLE | HOUSE FLY |
| S—n-propyl | 120 | 5 | 115 | 11 | 90 |
| O—ethyl | i | i | i | i | i |

Table III illustrates that with the compounds of this invention, O-ethyl-S-n-propyl is significantly more active than the O-ethyl-O-ethyl phosphates.

I claim:

1. Compounds of the formula:

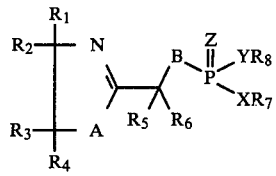

wherein:
A is O or S;
B is O, S or NH;
X is O or S
Y is S or NH;
Z is O or S;
$R_7$ and $R_8$ are individually $C_1$ to $C_6$ alkyl;

R₁, R₂, R₃ and R₄ are individually hydrogen, alkyl, halogen, haloalkyl, phenyl, phenyl substituted with one or more nitro, halogen, alkyl, trifluoroalkyl, cyano, alkoxy, and alkylthio groups; or R₁, R₂, R₃ and R₄ together form a 6-membered aromatic ring which is non-substituted or alkyl, alkoxy, alkylthio, halo, nitro, cyano, trifluoromethyl, phenoxy, phenyl, trifluoromethoxy, phenylthio, alkylcarbonyl, alkoxycarbonyl, alkylaminocarbonyl substituted;

R₅ is hydrogen, cyano, alkyl, or alkynyl;

R₆ is non-substituted phenyl or alkyl, alkylthio, alkoxy, halo, nitro, cyano, alkylamino, dialkylamino, trifluoromethyl, phenoxy, phenylthio, halophenoxy, or alkynyl substututed phenyl.

2. A compound in accordance with claim 1 wherein:
X is O;
Y is S;
R₅ is hydrogen.

3. A compound in accordance with claim 2 wherein:
B is oxygen;
R₆ is a halo-substituted benzene ring;
R₈ is n-propyl; and
R₇ is ethyl.

4. O-[alpha-(2-benzothiazolyl)-2-chlorobenzyl]-O-ethyl-S-n-propyl thiophosphate.

5. O-[alpha-(2-benzothiazolyl)-2,4-dichlorobenzyl]-O-ethyl-S-n-propyl thiophosphate.

6. O-[alpha-(2-benzoxazolyl)-2-chlorobenzyl]-O-ethyl-S-n-propyl thiophosphate.

7. O-[alpha-(2-benzoxazolyl)-2,4-dichlorobenzyl]-O-ethyl-S-n-propyl thiophosphate.

8. O-[alpha-(2-benzoxazolyl)-3,4-dichlorobenzyl]-O-ethyl-S-n-propyl thiophosphate.

9. O-[alpha-(2-benzoxazolyl)-2,6-dichlorobenzyl]-O-ethyl-S-n-propyl thiophosphate.

10. O-[alpha-(2-benzothiazolyl)-2-nitrobenzyl]-O-ethyl-S-n-propyl thiophosphate.

11. An insecticidal and miticidal composition comprising an acceptable carrier and as the active toxicant, a pesticidally effective amount of a compound of the formula:

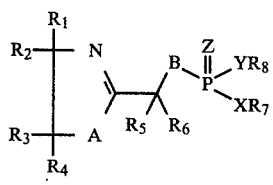

wherein:
A is O or S;
B is O, S or NH;
X is O or S;
Y is S or NH;
Z is O or S;
R₇ and R₈ are individually C₁ to C₆ alkyl;
R₁, R₂, R₃ and R₄ are individually hydrogen, alkyl, halogen, haloalkyl, phenyl, phenyl substituted with one or more nitro, halogen, alkyl, trifluoroalkyl, cyano, alkoxy, and alkylthio groups; or R₁, R₂, R₃ and R₄ together form a 6-membered aromatic ring which is non-substituted or alkyl, alkoxy, alkylthio, halo, nitro, cyano, trifluoromethyl, phenoxy, phenyl, trifluoromethoxy, phenylthio, alkylcarbonyl, alkoxycarbonyl, alkylaminocarbonyl substituted;

R₅ is hydrogen, cyano, alkyl, or alkynyl;

R₆ is non-substituted phenyl or alkyl, alkylthio, alkoxy, halo, nitro, cyano, alkylamino, dialkylamino, trifluoromethyl, phenoxy, phenylthio, halophenoxy, or alkynyl substututed phenyl.

12. A composition in accordance with claim 11 wherein:
X is O;
Y is S;
R₅ is hydrogen.

13. A composition in accordance with claim 12 wherein:
B is oxygen;
R₆ is a halo-substituted benzene ring;
R₈ is n-propyl; and
R₇ is ethyl.

14. An insecticidal and miticidal composition comprising an acceptable carrier and as the active toxicant, a pesticidally effective amount of O-[alpha-(2-benzothiazolyl)-2-chlorobenzyl]-O-ethyl-S-n-propyl thiophosphate.

15. An insecticidal and miticidal composition comprising an acceptable carrier and as the active toxicant, a pesticidally effective amount of O-[alpha-(2-benzothiazolyl)-2,4-dichlorobenzyl]-O-ethyl-S-n-propyl thiophosphate.

16. An insecticidal and miticidal composition comprising an acceptable carrier and as the active toxicant, a pesticidally effective amount of O-[alpha-(2-benzoxazolyl)-2-dichlorobenzyl]-O-ethyl-S-n-propyl thiophosphate.

17. An insecticidal and miticidal composition comprising an acceptable carrier and as the active toxicant, a pesticidally effective amount of O-[alpha-(2-benzoxazolyl)-2,4-dichlorobenzyl]-O-ethyl-S-n-propyl thiophosphate.

18. An insecticidal and miticidal composition comprising an acceptable carrier and as the active toxicant, a pesticidally effective amount of O-[alpha-(2-benzoxazolyl)-3,4-dichlorobenzyl]-O-ethyl-S-n-propyl thiophosphate.

19. An insecticidal and miticidal composition comprising an acceptable carrier and as the active toxicant, a pesticidally effective amount of O-[alpha-(2-benzoxazolyl)-2,6-dichlorobenzyl]-O-ethyl-S-n-propyl thiophosphate.

20. An insecticidal and miticidal composition comprising an acceptable carrier and as the active toxicant, a pesticidally effective amount of O-[alpha-(2-benzothiazolyl)-2-nitrobenzyl]-O-ethyl-S-n-propyl thiophosphate.

21. A method of controlling insects and mites which comprises subjecting them to an insecticidally or miticidally effective amount of a compound of the formula:

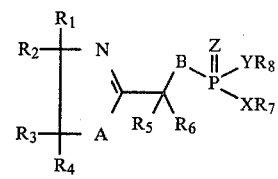

wherein:
A is O or S;
B is O, S or NH;
X is O or S;

Y is S or NH;
Z is O or S;
$R_7$ and $R_8$ are individually $C_1$ to $C_6$ alkyl;
$R_1$, $R_2$, $R_3$ and $R_4$ are individually hydrogen, alkyl, halogen, haloalkyl, phenyl, phenyl substituted with one or more nitro, halogen, alkyl, trifluoroalkyl, cyano, alkoxy, and alkylthio groups; or
$R_1$, $R_2$, $R_3$ and $R_4$ together form a 6-membered aromatic ring which is non-substituted or alkyl, alkoxy, alkylthio, halo, nitro, cyano, trifluoromethyl, phenoxy, phenyl, trifluoromethoxy, phenylthio, alkylcarbonyl, alkoxycarbonyl, alkylaminocarbonyl substituted;
$R_5$ is hydrogen, cyano, alkyl, or alkynyl;
$R_6$ is non-substituted phenyl or alkyl, alkylthio, alkoxy, halo, nitro, cyano, alkylamino, dialkylamino, trifluoromethyl, phenoxy, phenylthio, halophenoxy, or alkynyl substututed phenyl.

22. A composition in accordance with claim 21 wherein:
X is O;
Y is S;
$R_5$ is hydrogen.

23. A method in accordance with claim 22 wherein:
B is oxygen;
$R_6$ is a halo-substituted benzene ring;
$R_8$ is n-propyl; and
$R_7$ is ethyl.

24. A method of controlling insects and mites which comprises subjecting them to an insecticidally or miticidally effective amount of O-[alpha-(2-benzothiazolyl)-2-chlorobenzyl]-O-ethyl-S-n-propyl thiophosphate.

25. A method of controlling insects and mites which comprises subjecting them to an insecticidally or miticidally effective amount of O-[alpha-(2-benzothiazolyl)-2,4-dichlorobenzyl]-O-ethyl-S-n-propyl thiophosphate.

26. A method of controlling insects and mites which comprises subjecting them to an insecticidally or miticidally effective amount of O-[alpha-(2-benzoxazolyl)-2-chlorobenzyl]-O-ethyl-S-n-propyl thiophosphate.

27. A method of controlling insects and mites which comprises subjecting them to an insecticidally or miticidally effective amount of O-[alpha-(2-benzoxazolyl)-2,4-dichlorobenzyl]-O-ethyl-S-n-propyl thiophosphate.

28. A method of controlling insects and mites which comprises subjecting them to an insecticidally or miticidally effective amount of O-[alpha-(2-benzoxazolyl)-3,4-dichlorobenzyl]-O-ethyl-S-n-propyl thiophosphate.

29. A method of controlling insects and mites which comprises subjecting them to an insecticidally or miticidally effective amount of O-[alpha-(2-benzoxazolyl)-2,6-dichlorobenzyl]-O-ethyl-S-n-propyl thiophosphate.

30. A method of controlling insects and mites which comprises subjecting them to an insecticidally or miticidally effective amount of O-[alpha-(2-benzothiazolyl)-2-nitrobenzyl]-O-ethyl-S-n-propyl thiophosphate.

* * * * *